United States Patent
Difiore

(10) Patent No.: US 8,523,798 B2
(45) Date of Patent: *Sep. 3, 2013

(54) METHOD FOR MEASURING RECIRCULATION IN CATHETERS

(75) Inventor: Attilio E. Difiore, Taylorsville, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 412 days.

This patent is subject to a terminal disclaimer.

(21) Appl. No.: 12/839,272

(22) Filed: Jul. 19, 2010

(65) Prior Publication Data
US 2010/0280805 A1 Nov. 4, 2010

Related U.S. Application Data

(63) Continuation of application No. 10/986,400, filed on Nov. 10, 2004, now Pat. No. 7,758,530.

(51) Int. Cl.
*A61M 37/00* (2006.01)
*C02F 1/44* (2006.01)

(52) U.S. Cl.
USPC .......... 604/4.01; 604/5.01; 210/739; 210/740

(58) Field of Classification Search
USPC ............... 604/4.01, 5.01, 5.04, 6.05, 6.06; 210/645, 646, 739, 746; 422/44
See application file for complete search history.

(56) References Cited

U.S. PATENT DOCUMENTS

| | | | |
|---|---|---|---|
| 5,588,959 | A | 12/1996 | Ahmad et al. |
| 5,595,182 | A | 1/1997 | Krivitski |
| 5,644,240 | A | 7/1997 | Brugger |
| 5,685,989 | A | 11/1997 | Krivitski et al. |
| 6,167,765 | B1 | 1/2001 | Weitzel |
| 6,189,388 | B1 | 2/2001 | Cole et al. |

OTHER PUBLICATIONS

U.S. Appl. No. 10/986,400, filed Nov. 10, 2004 Notice of Allowance dated Mar. 15, 2010.
Aug. 12, 2009 Non-Final Office Action in U.S. Appl. No. 10/986,400, filed Nov. 10, 2004.

*Primary Examiner* — Leslie Deak
(74) *Attorney, Agent, or Firm* — Rutan & Tucker, LLP

(57) ABSTRACT

A system and method for measuring recirculation of blood in a catheter designed for implantation in a human is described. In one variation, the system comprises an artificial circulatory system and an ultrasonic detection device for measuring and comparing the density of a circulated blood simulant with a later introduced bolus saline. The system may be configured to simulate a human heart by providing the flow, pressure and dimensions of a typical human heart. In addition to simulating the circulatory system of a normal human heart, the system may also be configured to simulate particular negative conditions of a patient, such as stenotic condition, which would affect the recirculation measurement.

20 Claims, 2 Drawing Sheets

METHOD FOR MEASURING RECIRCULATION IN CATHETERS

CROSS-REFERENCE TO RELATED APPLICATIONS

This application is a continuation of U.S. patent application Ser. No. 10/986,400, filed Nov. 10, 2004, now U.S. Pat. No. 7,758,530, which is incorporated by reference in its entirety into this application.

BACKGROUND OF THE INVENTION

A system that effectively measures a catheter's performance in vitro is useful in designing catheters for implantation in patients. Because various physiological factors (e.g., blood flow, blood pressure, vessel dimensions, etc.) impact the operation of a given catheter, to effectively compare the performance of catheters with different design parameters, one would need a simulation system that provides user control of the physiological parameters. It may also be beneficial to have a simulation system that would allow the design engineers to set a baseline to measure and compare the performance of different catheter designs.

Thus, an in vitro system that provides design engineers a controlled environment to test various design parameters and optimize the performance of catheters is desirable. In particular, a system that properly simulates the flow and pressure characteristics in a human heart is useful for testing dialysis catheters. One of the key parameters that govern the performance of a dialysis catheter is the recirculation rate. The measurement of the recirculation of blood is an important variable with respect to dialysis catheters because it is advantageous to know the amount of cleaned blood that is entering back into the catheter and mixing with the "dirty" blood. The ability to test and effectively predict the recirculation rate of the catheter in a simulated implant condition allows the engineers to design a catheter that would minimize recirculation and improve the efficiency of the catheter. However, since the recirculation rate in vivo is affected by various physiological factors, a system that can provide effective recirculation rate measurements needs to properly simulate the various physiological factors (e.g., blood flow rate, blood pressure, dimensions of the vessel, etc.).

Over the years, various systems have been designed for measuring recirculation of blood in dialysis catheters. Examples of some of these designs are disclosed in U.S. Pat. No. 5,588,959, titled "HEMODIALYSIS RECIRCULATION MEASURING METHOD" issued to Ahmad et al., dated Dec. 31, 1996; U.S. Pat. No. 5,644,240, titled "DIFFERENTIAL CONDUCTIVITY HEMODYNAMIC MONITOR" issued to Brugger, dated Jul. 1, 1997; U.S. Pat. No. 5,685,989, titled "METHOD AND APPARATUS TO MEASURE BLOOD FLOW AND RECIRCULATION IN HEMODIALYSIS SHUNTS" issued to Krivitski et al., dated Nov. 11, 1997; U.S. Pat. No. 6,167,765 B1, titled "SYSTEM AND METHOD FOR DETERMING THE FLOW RATE OF BLOOD IN A VESSEL USING DOPLLER FREQUENCY SIGNALS" issued to Weitzel, dated Jan. 2, 2001; U.S. Pat. No. 6,189,388 B1, titled "ACCESS FLOW MONITORING USING REVERSAL OF NORMAL BLOOD FLOW" issued to Cole et al., dated Feb. 20, 2001; each of which is incorporated herein by reference in its entirety.

Many of the existing systems do not effectively simulate the blood flow (e.g., vortex flow due to heart chamber shape and vessel wall characteristics, etc.) and blood pressure (blood pressure change due to the cycling of the heartbeat, etc.) changes surrounding the catheter in an implanted condition. Since the amount of recirculation is affected by the turbulence and various fluid dynamics at the distal end of a dialysis catheter due to the vessel and the heart's physiological characteristics, a simulation system that can simulate these characteristics and variables may be more effective in measuring the actual recirculation rate in an implanted environment. Thus, it may be desirable to provide a realistic cardiovascular simulation environment for the testing of dialysis catheters. It may also be beneficial to allow the operator to control the fluid flow, pressure dynamics, and physical characteristics of the simulation system, and preset these parameters to conditions that simulate the environmental condition in which the catheter would be utilized in an actual human body.

BRIEF SUMMARY OF THE INVENTION

Accordingly, described herein is a system and method for measuring recirculation of blood in a dialysis catheter. An artificial circulatory system is provided to simulate the environment in which the distal end of an implanted dialysis catheter would experience in a human circulatory system. In one variation, the system simulates the human circulatory system for catheter testing by providing flow, pressure and physical dimension characteristics at the superior vena cava and right atrium of a human heart. Catheters with different design parameters may be inserted into the simulation system with the distal end of each catheter placed in the superior vena cava and/or the atrium for testing. The performance of the catheter may also be tested in relation to the position of the catheter inside the simulated system. For example, certain catheter design may provide better performance when its distal tip is placed within the superior vena cava, while others may function more efficiently when the distal end of the catheter is placed within the right atrium. The recirculation rate measurement may be achieved by ultrasonically comparing the density of blood simulant with a later introduced bolus of saline.

In one aspect of the invention, the system is configured for measuring the effective recirculation rate of a dialysis catheter. This mock system need not emulate the complete cardiovascular system, since the system need only simulate the environment around the superior vena cava and the right atrium where the input and output ports of a dialysis catheter is typically positioned in an actual patient. The system may be configured to maintain as constant the key physiological factors in the simulated system, namely circulatory volumetric flow, blood pressure, fluid viscosity, heart rate and catheter tip placement location such that a baseline may be establish to compare the performance of the various catheters being tested with the system.

The system may be configured to simulate the condition experienced by a dialysis catheter implanted in a normal human heart. In addition, the system may also be configured to simulate particular negative conditions of a patient's circulatory condition, such as stenosis, which would affect recirculation rate of a catheter.

These and other embodiments, features and advantages of the present invention will become more apparent to those of ordinary skill in the art when taken with reference to the following more detailed description of the invention in conjunction with the accompanying drawings that are first briefly described.

DETAILED DESCRIPTION OF THE INVENTION

The following detailed description should be read with reference to the drawings, in which like elements in different drawings are identically numbered. The drawings, which are not necessarily to scale, depict selected preferred embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Before describing the present invention, it is to be understood that unless otherwise indicated this invention need not be limited to testing dialysis catheters. One of ordinary skill in the art would appreciate that other variations of catheters may also be inserted into the simulation system described herein for testing and measurement. Moreover, it should be understood that embodiments of the present invention may be applied in combination with various fluid delivery device and/or blood processing system (e.g., dialysis pump, blood filters, etc.) for testing of a catheter's performance. It must also be noted that, as used in this specification and the appended claims, the singular forms "a," "an" and "the" include plural referents unless the context clearly dictates otherwise. Thus, for example, the term "a port" is intended to mean a single port or a combination of ports, "a fluid" is intended to mean one or more fluids, or a mixture thereof.

Figure 1:
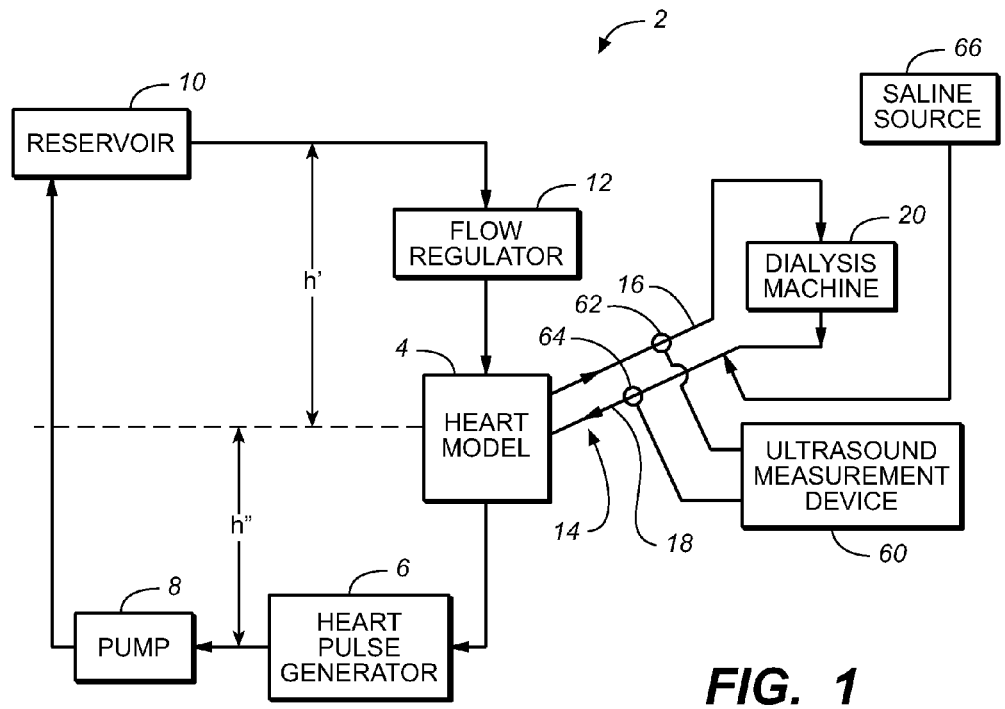
FIG. 1 is a block diagram illustrating one variation of the cardiovascular simulation system. The system as shown may be implemented to test a dialysis catheter's recirculation rate.

In one variation, the cardiovascular simulation system 2 comprises a heart model 4, a heart pulse generator 6, a fluid pump 8, a reservoir 10, and a flow regulator 12 as shown in FIG. 1. Also shown in FIG. 1, is the fluid flow paths of a dual lumen dialysis catheter 14 inserted inside the heart model 4 for drawing fluids from, and returning fluids to the heart model 4. A machine with a fluid pump is used to aspirate fluid through the inflow lumen (i.e., the arterial line) 16 in the catheter and to infuse the extracted fluid through the outflow lumen (i.e., the venous line) 18 in the catheter back into the heart model. In this case, a dialysis machine 20 is implemented to extract and return fluid through the dual lumen dialyses catheter 14.

Figure 2:
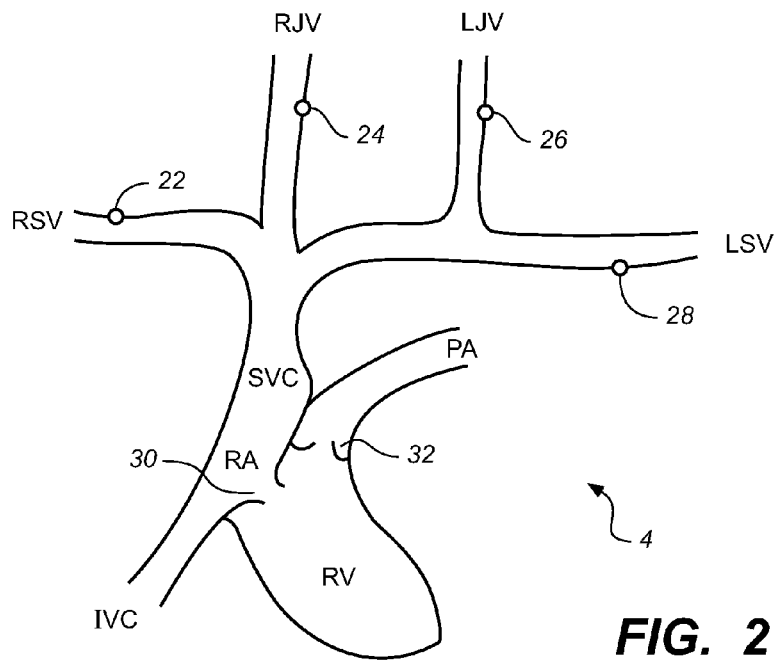
FIG. 2 illustrates the heart model implemented in the configuration shown in FIG. 1.

In this example, the heart model 4 comprises a glass model of the right side of the heart, including, right atrium (RA), right ventricle (RV), left jugular vein (LJV), right jugular vein (RJV), left subclavian vein (LSV), right subclavian veins (RSV), superior vena cava (SVC), inferior vena cava (IVC), and the pulmonary artery (PA), as shown in FIG. 2. Catheter insertion sites 22, 24, 26, 28 may be provided on both subclavian veins as well as both jugular veins. Valves may be provided to simulate the tricuspid valve 30 and the pulmonary valve 32. For example, typical tissue valves or mechanical valves that are routinely used in surgical repair of damaged heart valves may be implemented in the heart model 4 to enhance the simulation system 2. An optional release valve may be provided on the right atrium. In addition, a pressure gauge or pressure sensor may be connected or attached to the glass heart model to measure pressure inside the pulmonary artery. The pressure information detected by the pressure sensor may be utilized by a feedback controller to adjust the overall pressure in the simulated heart model. Pressure sensor, detectors, or gauges may also be placed in other chambers or vessels in the heart model to provide feedback to the operator or the system controller. Although a glass heart model is describe above, the heart model may also comprise other materials (e.g., plastic, hard or soft polymer, elastic materials, metal or metal alloyed, etc.). For example, the heart model may comprise a compliant material such as silicon to provide similar elastic characteristics that is present in a real human heart.

The fluid in the heart model 4 outputs from the pulmonary artery and the outflow fluid feed into the heart pulse generator 6. This device 6 interrupts blood flow through the simulation system 2 by generating a pulse equivalent to standard resting heart rate of 72 beats per minute. The user may adjust the pulse rate to a higher or lower level if desired. The output of the heart pulse generator 6 flows into a fluid pump 8. In this example, a gear pump 8 connected to an electronic controller drives the fluid flow and maintains the fluid circulation in the simulation system 2. The fluid being circulated in the system may be a blood simulant. In one variation, the blood simulant has a viscosity similar to human's blood. For example, the blood simulant may comprise a glycerin/water mixture with a viscosity of about 3.5 cps at 20 degree Celsius. 3.5 cps is the average blood viscosity in normal adults. The blood simulant may be prepared by mixing glycerin and water in a 51% to 49% mixture ration. A viscometer may be used to determine the viscosity of the mixture, and glycerin or water may be added to achieve the desired viscosity. In one variation, the mixture has a viscosity in the range of approximately 3.5 to 4.0 cps. In another variation, the blood simulant may be prepared with saline and other large molecular weight molecules, such as proteins. The blood stimulant may also comprise of a variety of fluid and/or chemical compositions that are well known to one of ordinary skill in the art for simulating human blood.

Although in this example, a heart pulse generator 6 and a gear pump 8 combination is used to drive the circulatory flow and provide the pulsating characteristics of a human circulatory flow, one of ordinary skill in the art would appreciate that a single pulsating or intermittent fluid pump (e.g., electromechanical driven pulsatile pump, etc.), or a combination of other fluid transfer/attenuation devices may be used to drive the circulatory flow in the simulation system. The output of the fluid pump 8 feeds into a reservoir 10. The reservoir 10 holds a supply of fluid to be circulated through the simulation system 2. In this example, the reservoir 10 contains approximately 7 liters of blood simulant solution.

Figure 3:
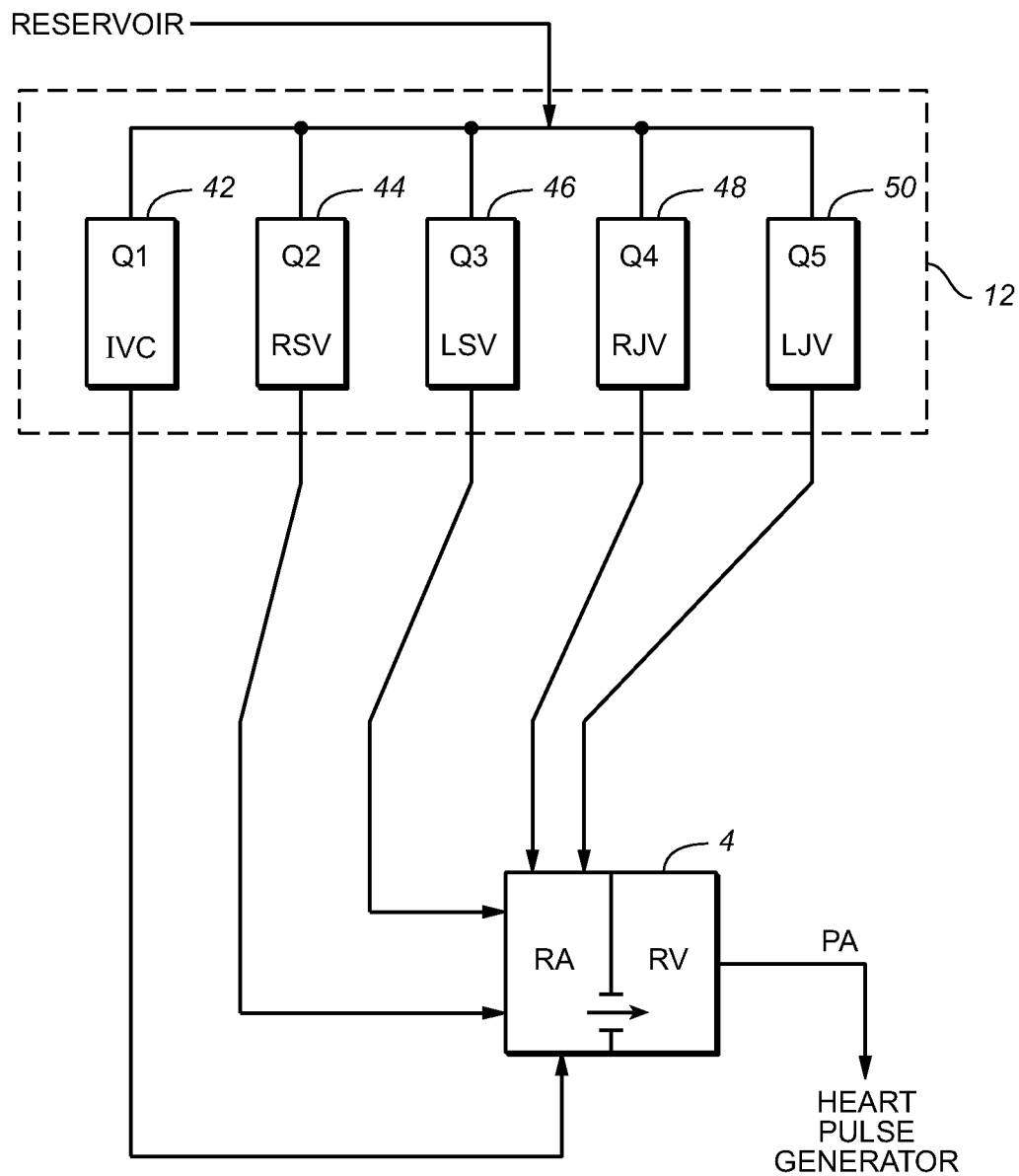
FIG. 3 is a block diagram illustrating the detailed fluid flow paths from the flow regulator to the heart model shown in FIG. 1.

The output of the reservoir 10 feeds into a flow regulator 12. The flow regulator 12 comprises a manifold with a plurality of valves, which allow the user to control the rate of fluid flow into various inputs on the heart model. In FIG. 3 the connection between the flow regulator 12 and the heart model 4 is shown in detail. The output of the first valve 42 supplies fluid to the IVC of the heart model 4 and its flow rate is represented by Q1. The output of the second valve 44 supplies fluid to the RSV of the heart model 4 and its flow rate is represented by Q2. The output of the third valve 46 supplies fluid to the LSV of the heart model 4 and its flow rate is represented by Q3. The output of the fourth valve 48 supplies fluid to the RJV of the heart model 4 and its flow rate is represented by Q4. The output of the fifth valve 50 supplies fluid to the LJV of the heart model 4 and its flow rate is represented by Q5. The flow rate for each of the valves, Q1, Q2, Q3, Q4, and Q5 may be adjusted depending on the operator's desire. For example, to simulate the circulatory system of a normal adult, one may set vales on the manifold to provide the following outputs, Q1=1.2 liter/min, Q2=1.0 liter/min, Q3=1.0 liter/min, Q4=0.9 liter/min, and Q5=0.9 liter/min. Thus, the total flow of the system Qt is 5 liter/min (Qt=Q1+Q2+Q3+Q4+Q5=5 liter/min). A typical human adult has a total circulatory flow rate of about five to six liters per minute.

A catheter may be tested in this simulation system by inserting the distal portion of the catheter into the system. For example, the system may be configured to test a dialysis catheter as shown in FIG. 1. A typical dialysis catheter has two lumens and each lumen has a port at the distal portion of the catheter. One of the lumen (i.e., the inflow lumen) is used for diverting blood from the circulatory system for processing, and the other (i.e., the outflow lumen) is used to reintroduce the processed blood back into the circulatory system. Since the outflow port and the inflow port are both located at the distal portion of the catheter, a portion of the processed blood exiting the outflow port may be recaptured by the suction at the inflow port and then processed again. If the catheter is poorly designed, a significant portion of the processed blood may be recirculated and redundantly processed. This results in a significant decrease in the efficiency of the dialysis process. In addition, physical features and characteristics of the tissues surrounding the catheter may cause local turbulence in flow and effect local fluid dynamics which can affect the amount of recirculation in the catheter.

To test the recirculation rate of a given catheter, the catheter may be inserted into the heart model through one of the access ports 22, 24, 26, 28 on the heart model 4, as seen on FIG. 2. The distal end of the catheter is advanced toward the right ventricle (RV) of the heart model. Typically, the inflow port of the dialysis catheter is placed just proximal to the superior vena cava (SVC). In another variation, one may also advance the distal tip of the catheter deep into the right atrium (RA). The proximal end of the catheter is connected to a dialysis machine. A dialysis pump in the dialysis machine drives the fluid flow in the dialyses catheter which aspirates blood through the inflow port of the catheter and infuses the processed blood through the outflow port of the catheter. For the purpose of testing recirculation, the system may be configured with only a fluid pump (e.g., peristaltic pump, dialysis pump, centrifugal pump, rotary blood pump, etc.) without the use of blood filters to direct fluid flow through the catheter.

In order to compare the results for different catheters being tested, it may be desirable to place a marker on the glass heart model 4 such that the operator can position each of the tested catheters at the identical position. For example, the operator may measure all the catheters from the distal end of the catheter and provide proper marking so as to ensure that the placement of the inflow port is always in the same location in the heart model between various test catheters. In addition, one may further position the catheter such that the outflow port always faces away from the wall of the right atrium. In another variation, one may align the various catheters by positioning each of the catheters to be tested such that the catheter's distal end is place at the same position within the heart model during testing.

In this variation, an ultrasound measurement device 60 is used to measure recirculation. As seen in FIG. 1, one ultrasonic sensor 62 is placed on the catheter's inflow path 16, and a second ultrasonic sensor 64 is placed on the catheter's outflow path 18. A bolus of saline is injected into the outflow path 18 (i.e., venous line) upstream of the sensor 64 to start the test sequence. A saline drip 66 may be implemented as a control mechanism with which a bolus of saline is administered into the simulation system. In another variation, a syringe may be used to inject a bolus of saline. Since the saline has a much lower density then the blood simulant in the simulation system, the saline will dilute the blood simulant. Based on the dilution curve detected by the two sensors 62, 64, the rate of recirculation is then calculated. In another variation, other measurement devices may be implemented with the artificial circulatory system described herein to measure catheter performance. For example, a temperature monitor may be used to determine recirculation rate by measuring the temperature changes in the inflow and outflow line of the catheter. In this case, a cold or hot saline solution may be injected into the circulatory system through the catheter for recirculation measurement.

The ultrasonic sensors 62, 64 monitor the rate of the blood simulant flow in and out of the dialysis catheter 14. The ultrasonic sensors 62, 64 may also monitor ultrasound velocity in the blood simulant. The ultrasound velocity is affected by the glycerin concentration: the greater the concentration, the faster ultrasound will travel in it. By introducing a bolus of isotonic saline into the blood simulant, the glycerin concentration is diluted and ultrasound velocity is decreased. The reduced ultrasound velocity is recorded by the sensors, and a computer in the ultrasonic measurement device converts these data into conventional dilution curves. When the saline is introduced into the catheter's outflow line 18, it passes the outflow sensor 64, producing an outflow indicator dilution curve. The recirculation carries portion of the diluted blood simulant back into the inflow line 16. Thus, this dilution is immediately be detected by the sensor 62 on the inflow line 16 and produce a second indicator dilution curve. Recirculation may be calculated as a ratio of the area under the inflow curve to the area under the outflow curve. Although in the above example a bolus of saline is used to initiate the test sequence, other fluid solutions that can increase or decrease the density of the blood simulant may also be used, as long as the administration of the bolus solution results in changes in density that can be detected by the ultrasound measurement device.

Although the heart model 4, shown in FIG. 2, comprising only the right atrium and right ventricle is described above, one of ordinary skill in the art would appreciate, in light of the description herein, that a heart models having all four chambers, right atrium, right ventricle, left atrium, and left ventricle, may also be used. In addition, the heart models with modified dimensions or flow characteristics may also be implemented to simulate various circulatory diseases. For example a heart model with an enlarged ventricle chamber may be implemented to simulate a symptom that is common in left ventricular hypertrophy. The paths between the various heart chambers may be narrowed to simulate a defective heart valve. In another variation, a valve with appropriate flow resistance characteristics may also be implanted in the heart model to simulate a defective heart valve. In another variation, flow resistance, either at the output of the heart model or downstream from the heart model, may be increased to simulate aortic stenosis. In yet another variation, a narrowing of the superior vena cava in the heart model may be implemented to simulate venous stenosis. Furthermore, other components of the simulation system may also be adjusted to provide improved circulatory disease simulations. For example, the output flow rate of the fluid pump may be decreased to simulate a failing heart. The fluid pressure inside the heart model may be increased to simulate hypertension.

Furthermore, referring to FIG. 1, the height displacement h' between the reservoir 10 and the heart model 4, and the height displacement h" between the heart model 4 and the pump 8, may be adjusted as necessary to simulated different physiological conditions. By changing the position of the reservoir with respect to the SVC atrial junction, pressures within the atrium can be increased or decreased. By moving the reservoir higher, or lower the heart model with respect to the reservoir, h' becomes larger, and the pressure within the atrium is increased, simulating physiological conditions of increased atrial pressure (e.g., hypertension, AV valve stenosis, etc.). In another variation, by changing the reservoir position in the opposite direction, bringing the reservoir closer to the atrium in the model, h' becomes smaller, and the pressure in the atrium is reduced, which may represent a patient in the sitting or slightly inclined position. These low pressures (0 psi and <0 psi) may represent any number of positions the patient can be found in during vascular access procedures.

An exemplary approach illustrating the use of fluid density measurement to determine recirculation rate in a catheter is set forth below.

A blood simulant is prepared by mixing glycerin and water in a 51% to 49% mixture ratio to obtain 6-7 liters of fluid. An 18 mL sample of mixture is taken and viscosity is measured using a Cole Parmer 98936 series viscometer. The viscosity of the mixture is adjusted by adding either glycerin or water to obtain a mixture of viscosity in the range of approximately 3.5 to 4.0 cps. Once the blood simulant is prepared, the reservoir 10 with the blood simulant may be placed at the same elevation as the flow regulator 12. The hoses traveling from the fluid pump 8 and to the flow regulator 12 are then inserted into the reservoir 10, at which point one may check to ensure that the atrium relief valve located on the right atrium of the heart model and the system drain valve are closed (a system drain valve may be provided on the inflow path to the inferior vena cava for draining fluid from the simulation system).

The test catheter is inserted through one of the catheter insertion sites on the heart model, the catheter is primed with blood simulant from the reservoir using a syringe, and the extension legs are capped so that air cannot enter the system. The catheter may be rotated so that the port for the outflow lumen of the catheter is facing away from the atrium wall. The fluid pump may be set to an outflow rate of 5 liter/min. A variable fluid pump capable of supporting pump rates between 0 to 10 liter/min may be utilized to control the flow rate. The system is primed by first running the pump in the forward direction. Next, the pump is initiated to allow all lines in the system to fill and purge as much air out of the system as practical before shutting the pump off. The flow of the pump is then reversed to allow any remaining air in the system to exit into the fluid bath and is reset to the forward direction. The above steps may be repeated as needed to remove all the air from the system. If necessary, a syringe may be used on the atrium relief valve to remove air from the right atrium. Also, the pressure detector may be monitored to check pressure of fluid leaving the heart chambers.

The test catheter is connected to a dialysis machine and the dialysis pump is run until all the air has been purged from the dialysis system. The dialysis machine has an arterial line (i.e., inflow line) and a venous line (i.e., outflow line) that are connected to the corresponding inflow and outflow lumens of the catheter. The two ultrasound sensors from the ultrasound measurement device (Transonic Flow-QC Hemodialysis Monitor, Transonic System Inc.; the Transonic monitor comprises a laptop computer, the HD-01 monitor, and a set of matched ultrasound sensors) are connected to the venous and arterial lines (this device is able to display the volumetric flow rate of the dialysis pump). The dialysis pump flow rate is then adjusted to the desired value and the heart pulse generator is turned on. After initiating the heart pulse simulator, the dialysis pump may be permitted to stabilize and may be readjusted where necessary to achieve the correct flow rate.

To begin the test, a bolus of saline is infused into the venous line of the dialysis machine upstream of the ultrasound sensor. The computer for the ultrasound measurement device indicates a bolus and begins its calculation. Thereafter, a read out appears on the display and indicates the recirculation. The system may then be permitted to stabilize for repeating the test, if necessary. To test another catheter, the fluid pump and the dialysis pump may be turned off, the first catheter may be removed from the dialysis lines and then removed from the insertion site. The new catheter is then primed with blood simulant and connected to the dialysis lines.

The catheters may be selected for testing by a randomly generated test matrix such that the results of the testing could be compared through statistical protocols that are well known to one of ordinary skill in the art. The above steps can be repeated until all the catheters in a given test group are evaluated. The catheters may be evaluated in a randomized format and measurements may be tested for part to part and system variability. Each of the catheter sample groups may also be tested through ANOVA analysis to demonstrate sample population differences.

This invention has been described and specific examples of the invention have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent covers those variations as well. Finally, all publications and patent applications cited in this specification are herein incorporated by reference in their entirety as if each individual publication or patent application were specifically and individually put forth herein.

What is claimed is:

1. A method of determining the amount of recirculation in a catheter having a inflow lumen and an outflow lumen, comprising:

placing a distal portion of the catheter into an artificial fluid loop, the fluid loop including a blood simulant with a viscosity of about 3.5 cps flowing in a pulsatile manner;

directing the blood simulant from the fluid loop to flow through into the catheter through the inflow lumen and out from the catheter through the outflow lumen;

measuring the density of blood simulant flowing into the outflow lumen;

measuring the density of blood simulant flowing out of the inflow lumen;

changing the density of blood simulant being returned through the outflow lumen by delivering a fluid of a higher density into the outflow lumen;

determining if there is a density change in blood simulant flowing through the outflow lumen;

determining if there is a density change in blood simulant flowing through the inflow lumen; and comparing changes in blood simulant density in the inflow lumen to changes in blood simulant density in the outflow lumen to determine the amount of recirculation in the catheter.

2. The method according to claim 1, wherein the density of blood simulant flowing through the catheter is changed by delivering a fluid of a lower density into the outflow lumen.

3. The method according to claim 2, wherein the density of blood simulant flowing through the catheter is changed by delivering a bolus of saline solution into the outflow lumen.

4. The method according to claim 1, wherein the blood simulant flowing through the fluid loop a mixture of a water and a glycerin solution.

5. The method according to claim 1, wherein the measuring steps further comprise measuring the changes in fluid density with an ultrasound measurement device.

6. A method of determining the amount of recirculation in a catheter having a inflow lumen and an outflow lumen, comprising:
   placing a distal portion of the catheter into an artificial fluid loop, the fluid loop including a blood simulant with a viscosity of about 3.5 cps flowing in a pulsatile manner, wherein the artificial fluid loop comprises a reservoir feeding blood simulant to a heart model, and a fluid pump is utilized to drive the blood simulant flow in the fluid loop, wherein the heart model comprises at least a right atrium chamber and a right ventricle chamber;
   directing the blood simulant from the fluid loop to flow through into the catheter through the inflow lumen and out from the catheter through the outflow lumen:
   measuring the density of blood simulant flowing into the outflow lumen;
   measuring the density of blood simulant flowing out of the inflow lumen;
   changing the density of blood simulant being returned through the outflow lumen;
   determining if there is a density change in blood simulant flowing through the outflow lumen;
   determining if there is a density change in blood simulant flowing through the inflow lumen; and
   comparing changes in blood simulant density in the inflow lumen to changes in blood simulant density in the outflow lumen to determine the amount of recirculation in the catheter.

7. The method according to claim 6, wherein the heart model further comprises a left atrium chamber, and a left ventricle chamber.

8. The method according to claim 6, wherein the heart model does not include a left atrium chamber and a left ventricle chamber.

9. The method according to claim 6, wherein the heart model further comprises a superior vena cava.

10. The method according to claim 9, wherein the heart model further comprises a left jugular vein, a right jugular vein, a left subclavian vein, a right subclavian vein, and an inferior vena cava.

11. The method according to claim 6, wherein the heart model comprises a glass material.

12. The method according to claim 6, wherein the heart model comprises an elastic material.

13. The method according to claim 6, wherein placement of the catheter comprises placing a distal end of the catheter in the right atrium of the heart model.

14. The method according to claim 13, wherein the density of blood simulant flowing through the catheter is changed by delivering a fluid of a lower density into the outflow lumen of the catheter.

15. The method according to claim 13, wherein the density of blood simulant flowing in the catheter lumens are determined by ultrasound.

16. A method of determining the amount of recirculation in a catheter having a inflow lumen and an outflow lumen, comprising:
   placing a distal portion of the catheter into an artificial fluid loop, the fluid loop including a blood simulant comprising a mixture of water and glycerin with a viscosity of about 3.5 cps flowing in a pulsatile manner;
   directing the blood simulant from the fluid loop to flow through into the catheter through the inflow lumen and out from the catheter through the outflow lumen;
   measuring the density of blood simulant flowing into the outflow lumen;
   measuring the density of blood simulant flowing out of the inflow lumen;
   changing the density of blood simulant being returned through the outflow lumen;
   determining if there is a density change in blood simulant flowing through the outflow lumen;
   determining if there is a density change in blood simulant flowing through the inflow lumen; and
   comparing changes in blood simulant density in the inflow lumen to changes in blood simulant density in the outflow lumen to determine the amount of recirculation in the catheter.

17. The method according to claim 16, wherein the density of blood simulant flowing through the catheter is changed by delivering a fluid of a lower density into the outflow lumen.

18. The method according to claim 17, wherein the density of blood simulant flowing through the catheter is changed by delivering a bolus of saline solution into the outflow lumen.

19. The method according to claim 16, wherein the density of blood simulant flowing through the catheter is changed by delivering a fluid of a higher density into the outflow lumen.

20. The method according to claim 16, wherein the measuring steps further comprise measuring the changes in fluid density with an ultrasound measurement device.

* * * * *